United States Patent [19]

Coan et al.

[11] Patent Number: 5,658,746
[45] Date of Patent: Aug. 19, 1997

[54] CELL SURFACE RECEPTOR COMPLEMENTATION

[75] Inventors: Michael H. Coan, El Cerrito; Cynthia J. Galloway, Emeryville; Vivian W. Lee, Richmond, all of Calif.

[73] Assignee: Bayer Corporation, Berkeley, Calif.

[21] Appl. No.: 552,432

[22] Filed: Nov. 3, 1995

Related U.S. Application Data

[63] Continuation of Ser. No. 641,211, Jan. 15, 1991, abandoned.

[51] Int. Cl.$^6$ .............. G01N 33/567; G01N 33/566; G01N 33/531; G01N 33/53
[52] U.S. Cl. .............. 435/7.24; 435/7.1; 435/7.21; 436/501; 436/547
[58] Field of Search ................... 435/7.1, 7.21, 435/7.24; 436/547, 501

[56] References Cited

U.S. PATENT DOCUMENTS

| | | | |
|---|---|---|---|
| 4,551,435 | 11/1985 | Liberti et al. | 436/541 |
| 4,664,911 | 5/1987 | Uhr et al. | 424/85 |
| 4,676,980 | 6/1987 | Segal et al. | 424/85 |
| 4,770,995 | 9/1988 | Rubin et al. | 435/7 |

OTHER PUBLICATIONS

Beutler et al., Science 229:869–871 (1985).
Silverstein et al., "Phagocytosis" in *Fundamental Immunology*, 2nd Ed., ed. Paul, W.E. (Raven Press Ltd., NY) 703–720 (1989).
Porter, A.G., "The Prospects for Therapy with Tumor Necrosis Factors and Their Antagonists," Trends Biotechnology 9:158–162. (1991).

*Primary Examiner*—Michael P. Woodward
*Attorney, Agent, or Firm*—James A. Giblin

[57] ABSTRACT

A method of controlling the amount of a biologically active substance binding to a cell surface having both receptors to the substance and receptors for the Fc domain of an antibody that can complex with the substance or other antibodies that can complex with the substance. By exploiting the generally more numerous Fc receptor sites, substance binding can be increased and/or controlled. Method contemplates controlling amounts of substances such as cytokines, hormones, and growth factors that are associated with cells such as monocytes, macrophages, granulocytes, B cells, T cells, and platelets. Method is illustrated using conjugated antibodies to tissue necrosis factor (TNF) to increase the binding of TNF to monocytes.

6 Claims, 1 Drawing Sheet

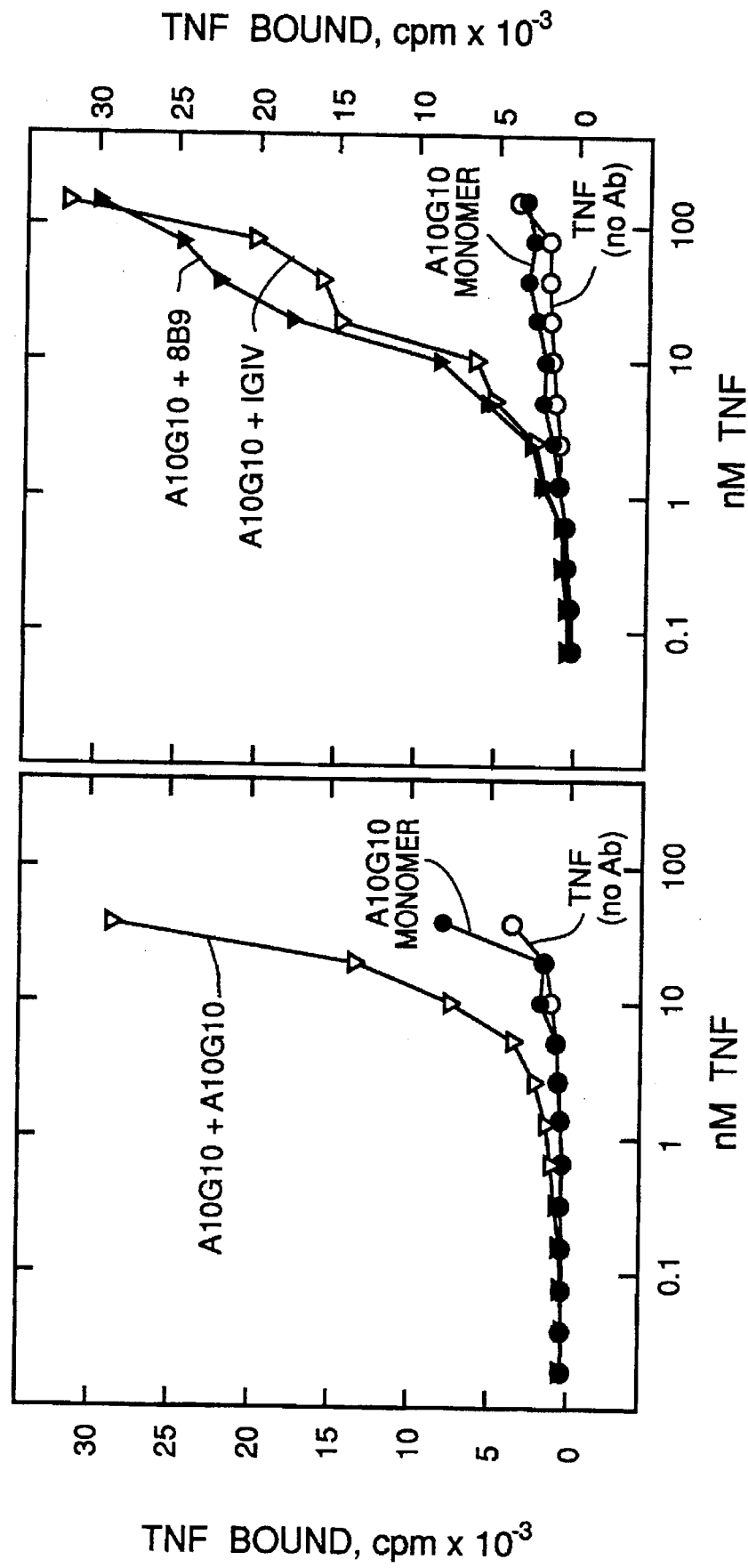

CELL SURFACE RECEPTOR COMPLEMENTATION

CROSS REFERENCE TO THE RELATED APPLICATIONS

This is a continuation of application Ser. No. 07/641,211, filed Jan. 15, 1991, now abandoned.

BACKGROUND OF THE INVENTION

1. Field

This disclosure is concerned generally with the binding of biologically active compounds to the surfaces of cells and specifically with a method of using cell receptors for the Fc domains of antibodies to control such binding.

2. Prior Art

Information about the binding of biologically active substances at the surfaces of cells has been increasing at a rapid rate, especially as new techniques for isolating and studying cell surface receptors sites have become available. While there is still much to be learned, it is now well known that many biological substances work or activate the generation of other substances by binding at so-called receptor sites at the surfaces of certain cells. More information on such cell receptor sites can be found, for example, in Alberts et al *Molecular Biology of the Cell*, 2nd ed, Garland Publishing, Inc. New York, 1989, pp 693–726.

In some cases, very small amounts of a biologically active substance can have a significant biological effect and very few cell surface receptors are needed. For example, in the case of the cytokine known as tumor necrosis factor (TNF), a very potent inflammatory mediator, it is known that the cells that respond to TNF have relatively few TNF receptor sites. See, for example, Beutler and Cerami, Ann. Rev. Immunol. 7:625–55, 1989. See also, U.S. Pat. No. 4,603,106 to Cerami et al, describing the isolation of a mediator referred to as cachetin and now known as TNF.

Among the other biologically active substances that have a relatively potent effect relative to their respective amounts are the various cytokines (e.g., IL1, IL2, and IL6), hormones (e.g., insulin, somatotropin, and adrenocorticotropic hormone, also known as ACTH) and growth factors (e.g., nerve growth factor, epidermal growth factor and fibroblast growth factor.) It should be understood that the above list of representative species is illustrative and by no means intended to be complete.

The function of all cells is governed by receptor interactions with these and other biologically active substances. These substances may act at a site distant from their site of origin (e.g., insulin made in the pancreas effects carbohydrate metabolism in the liver), or these substances may act locally, sometimes effecting the same cell which produces them (e.g., T cells both produce and respond to IL2) (See, for example, Alberts et al, pp 682–694, 1046–1047). Clearly, in the micro-environment of the cell surface, fluctuations in the amount of biologically active substances regulate cell function. In the case of potent cytokines and inflammatory mediators, high levels of these substances may have disastrous consequences; e.g., septic shock (Beutler and Cerami, Ann. Rev. Immunol. 7:625–55, 1989). In these cases it would be highly desirable to control the level of these substances in the micro-environment of the cell surface.

In cells where there are relatively few surface receptors for a given substance, the options available for influencing the amount of substance in the micro-environment of the cell surface are somewhat limited. However, it is known that many cells that have a limited number of specific receptors also have available receptors for the Fc domain of antibodies (See, for example, Mellman et al, J. Cell. Sci. Suppl. 9:45–65, 1988). In many cases, the number of these Fc domain receptors is many-fold greater than the limited number of substance receptors.

Taking into consideration the fact that some cells have receptor sites for both a given substance and the Fc domain of antibodies, we have now found methods for influencing the amount of substance in the micro-environment of such cells. This is done by exploiting the Fc receptors by using antibodies specific to the substance, or conjugated antibodies that include at least some antibodies specific to the substance. Details of our methods and examples using such antibodies are described below.

SUMMARY OF INVENTION

Our method of controlling the amount of binding of a substance to cell surfaces having a limited number of substance receptors and at least some receptors for the Fc domain of an antibody comprises the steps of (a) binding the Fc domains of antibodies or antibody conjugates which bind to the substance to at least some of the Fc receptors to form cells having an antibody-modified cell surface, and (b) contacting the cells of step (a) with a solution of the substance under conditions sufficient to permit binding of the substance to at least some of the cell surface substance receptors and available Fab domains of the antibodies.

In one embodiment, the antibodies bound to the cell surfaces at their Fc domains are conjugated with other antibodies, at least some of which bind to the substance. The antibodies between the cell surface and substance may be of conventional form or constructed chimeric type.

In one preferred embodiment, the conjugated antibodies comprise antibodies covalently bonded (e.g., by disulfide bonds) to other antibodies, at least some of which have sites that will combine with the substance.

The cells (e.g., monocytes, macrophages, granulocytes, B cells, T cells and platelets) must have surface receptors for both the substance and the Fc domain of the antibodies.

Our method of controlling substance binding provides a way to not only increase (or decrease) the net substance binding in the micro-environment of the cell surface, but it also permits control of the amount of that substance by controlling the amount of antibodies used. Thus it is possible that our method may have both diagnostic, therapeutic, and other applications.

In an illustrative example, we show how conjugated anti-TNF antibodies can be used to greatly increase the amount of TNF that can be bound to cells in a fluid environment including macrophage cells.

BRIEF DESCRIPTION OF THE FIGURES

The figures show two graphs (FIG. 1 and FIG. 2) illustrating how the amount of TNF binding to cells can be increased using the method of this disclosure.

SPECIFIC EMBODIMENTS

As used herein, the expression substance or biologically active substance refers to a compound having a biological effect in a living cell environment. Examples of such substances are the various cytokines such as TNF, IL1, IL2, and IL6; hormones such as insulin, somatotropin, and ACTH; and growth factors such as nerve growth factor, epidermal growth factor and fibroblast growth factor.

The cells include any cell that has receptors for both the substance and at least some receptors for the Fc domain of an antibody (e.g., macrophages, monocytes, granulocytes, B cells, T cells, platelets and the like).

The term control or controlling as used herein, refers to using the techniques disclosed herein to maintain, increase or decrease the amount of a biologically active substance in the environment of a living cell.

Antibody conjugates refers to antibodies which have been coupled to one another using covalent chemical bonds. The conjugates may comprise identical antibodies (homoconjugates) or non-identical antibodies, at least one of which has available Fab domains for binding substance (heteroconjugates).

Our method is illustrated in the examples below where we show a significant increase in TNF binding by monocytes using, in addition to the TNF receptors, conjugated anti-TNF antibodies.

Materials and Methods

To increase the amount of TNF bound to cells, living cells known as U937 cells were incubated with saturating concentrations of either monomeric anti-TNF or various conjugates containing this antibody. Then radiolabelled TNF was added to assess the effect of antibody incubation on TNF binding. More details on the methods we used are described below.

Cells and Cell Culture:

The human histiocytic lymphoma cell line U937 (ATCC CRL 1593) was grown in DME (Mediatech) supplemented with 10% fetal bovine serum (Hyclone) and 1 mM sodium pyruvate (Mediatech).

Antibodies:

The anti-TNF antibody is a murine monoclonal anti-human TNFα called A10G10 obtained from a deposited cell line having an ATCC accession number HB 9736. A human monoclonal anti-pseudomonas antibody (8B9), ATCC accession No. CRL 8833, and 10% human IgIV solution, pH 4.25 (Gamimune-N, Cutter Biological, Miles Inc.) were also used.

Antibody Conjugation:

The A10G10 antibodies were covalently coupled to either themselves, the 8B9 antibodies, or IgIV using the heterobifunctional cross-linker N-succinimidyl-3-(2-pyridyldithio) propionate (SPDP, Pierce). Following the general procedure of Cumber et al (Methods in Enzymology 112: 207–224, 1985), each member of the pair was first derivatized with SPDP. Then the SPDP-modified A10G10 was reduced and coupled to the second SPDP-modified protein by thiol-disulfide exchange.

The resulting conjugates were purified by gel filtration on Sephacryl® S-300 gel filtration media (Pharmacia, LKB). This product is a hydrophilic cross-linked copolymer of allyl dextran and N,N'-methylene bisacrylamide.

Iodination:

Human recombinant TNF was radiolabelled with $^{125}$I using iodogen (Fraker, P. J. and Speck, J. C. Biophys. Res. Comm. 80:849–857, 1978). Free iodine was removed by gel filtration on Sephadex® G-25 gel filtration media (Pharmacia, LKB). This media is a well-known cross-linked dextran.

TNF Binding Assay:

To measure the increase in TNF binding to U937 cells caused by the conjugates, U937 cells were harvested from culture and washed with DME containing 1.0% bovine serum albumin (DME/BSA). Then 1×10$^6$ U937 cells in 50 μl of DME/BSA were added to each well of a 96-well break-apart microtiter plate (Corning) which had been previously blocked with DME/BSA. To saturate antibody binding sites, 50 μl of 40 μg/ml antibody or conjugate was added to each well, making the final antibody concentration 20 μg/ml. After two hours at 4° C. with gentle mixing, unbound antibody was removed by washing the cells three times with cold DME/BSA. To detect TNF binding to the cells, $^{125}$I-TNF was added in serial two fold dilutions to each well. After incubation at 4° C. for two hours, the excess TNF was removed by washing three times with cold DME/BSA. Radioactivity bound to the cells was detected by counting the wells in a gamma counter (LKB 1282 COMPUGAMMA).

Discussion of the Figures

To determine if A10G10 monomers and high molecular weight conjugates of A10G10 caused an increase in TNF binding to the cell surface, U937 cells were incubated sequentially with antibody or conjugates, then with labelled TNF. As shown in FIG. 1, a relatively small amount of TNF binds to U937 cells in the absence of antibody. When the cells were incubated with A10G10 monomers, there was little difference in TNF binding. However, when the cells were incubated with a high molecular weight form of conjugated A10G10 antibodies made by covalently linking A10G10 to itself, the binding of TNF to U937 cells was strikingly increased, especially above a TNF concentration of 1 nM. As shown in FIG. 2, when A10G10 was covalently linked or conjugated to a different antibody, 8B9 antibodies or IGIV, the same increase in TNF binding was observed.

The increase in TNF binding observed in the presence of antibody conjugates is due to the binding of anti-TNF antibody to the cell surface via Fc receptors, which in turn increase the possible number of TNF binding sites on the cell. U937 cells, like other human monocytes and macrophages, express Fc receptors (Looney, et al Immunology 136:1641–1647, 1986). These receptors have a relatively low affinity for monomeric IgG, but a high affinity for multimeric antibodies of human and mouse origin (See, for example, Mellman et al, J. Cell Sci. Suppl. 9:45–65, 1988).

The anti-TNF antibody conjugates did not affect or increase TNF binding on cells which do not express Fc receptors. TNF bound via a conjugated antibody was degraded, consistent with the fate of antibody complexes bound to Fc receptors (Mellman et al, J. Cell Sci. Suppl. 9:45–65, 1988). While the binding of A10G10 monomers to the cells did not lead to a substantial increase in TNF binding, formation of an antigen-antibody complex before binding antibodies to the cell surface would also promote cell surface binding of antigen (Mellman et al, J. Cell Sci. Suppl. 9:45–65, 1988). Nevertheless, labelled A10G10 antibody did bind to the cells. In fact, A10G10 monomers and conjugates containing A10G10 competed for the same binding sites. Because an antibody of the same subclass, but different specificity also competed for A10G10 binding, the cell surface binding site is specific for the Fc domain of antibodies.

By using antibodies or preferably antibody conjugates which bind TNF to the cell surface via Fc receptors and lead to degradation of TNF, TNF is no longer available to exert its potent pleiotropic effects on other cells (See, for example, Beutler et al, Ann. Rev. Immunol. 7:625–55, 1989 to show the effects of TNF on other cells.). In fact, while the U937 cells used in this example carry both TNF and Fc receptors, any cells which expressed the appropriate Fc receptor will bind antibody or conjugated antibody, and if that antibody or conjugate contains some anti-substance antibody, the substance will be bound and prevented from reacting with its biological target regardless of origin.

Discussion

Given the above findings it has not escaped our attention that there are many potentially useful implications of this work. Monoclonal antibodies have been considered as potential therapeutics for the treatment of disease. For example, antibodies against IL2 receptor may inhibit the immune response after tissue transplantation. Using the methods described here to conjugate a human antibody to a mouse monoclonal antibody may enhance the therapeutic effectiveness of mouse monoclonal antibodies by increasing the ability of mouse antibodies to bind to human Fc receptors. More effective binding of mouse monoclonals to human Fc receptors would lead to faster clearance of the monoclonal antibody and the substance it binds from tissues. Then mouse monoclonal antibodies would be effective without the need for human monoclonal antibody development or chimerization of mouse monoclonal antibodies with human determinants.

The antigen-antibody reactions used in the method described can be exploited in a variety of fashions for therapeutic purposes. For example, an anti-hormone antibody or conjugate may be useful to control the excess amount of hormone produced by some tumors. An antibody against a drug or poison could be used to control overdoses, by quickly removing it from the circulation. An antibody against a cell surface determinant, for example CD4 or IL2 receptor, could be used to purge bone marrow of immune reactive cells before transplantation by promoting phagocytosis by Fc receptor-bearing cells.

While an Fc domain is necessary to link the conjugate and substance to an Fc receptor, the binding reaction which links the substance to an Fc domain need not be an antigen-antibody reaction. For example, an antibody engineered with the HIV-binding domain of CD4 would be expected to bind HIV and lead the virus to degradation in macrophages rather than infection of T cells. Any receptor, whether natural or synthesized, could be coupled to the Fc domain of an antibody and used to remove an excess of ligand from the circulation or tissues of interest. For example, an antibody coupled to recombinant $\alpha_1$-proteinase inhibitor, when delivered as an aerosol, could be an effective therapeutic in emphysema by causing removal of elastase by alveolar macrophages. Antibody coupling of $\alpha_1$-proteinase inhibitor and aerosol delivery may be particularly attractive because the recombinant non-glycosylated inhibitor is readily cleared from the circulation when administered.

Given the above examples, it is thought that numerous variations will occur. Accordingly, it is intended that the above examples should be construed as illustrative only and that the scope of the invention disclosed here should be limited only by the following claims.

We claim:

1. A method of controlling the amount of binding of a biologically active substance to cell surfaces having a limited number of substance receptors and a greater number of receptors for the Fc domain of an antibody, the method comprising the steps of (a) contacting the cell surfaces with a first solution comprising antibody conjugates which have available Fab domains for binding with the substance, under conditions sufficient to allow at least some of the Fc receptors on the cell surfaces to be bound by antibody conjugates, (b) washing unbound antibody conjugates from the cell surfaces, and (c) contacting the cell surfaces of step (b) with a second solution comprising the substance, under conditions sufficient to permit binding of the substance to at least some of the substance receptors and available Fab domains such that the amount of substance bound to the cell surfaces is greatly increased over that observed if antibody monomers are used in place of the antibody conjugates.

2. The method of claim 1 wherein the conjugated antibodies comprise antibodies covalently bonded to other antibodies at least some of which have available Fab domains for binding with the substance.

3. The method of claim 2 wherein the covalent binding is by covalent disulfide bonds.

4. The method of claim 1 wherein the substance is tumor necrosis factor, the antibodies comprise anti-tumor necrosis factor antibodies, and the cells are monocytes or macrophages.

5. The method of claim 4 wherein the conjugates are homoconjugates.

6. The method of claim 5 wherein the conjugates are heteroconjugates.

* * * * *